United States Patent [19]

Paciorek et al.

[11] 4,166,071

[45] Aug. 28, 1979

[54] MONOPHOSPHA-S-TRIAZINES

[75] Inventors: Kazimiera L. Paciorek, Corona del Mar; Reinhold H. Kratzer; Jacquelyn Kaufman, both of Costa Mesa; Thomas I. Ito, Fountain Valley, all of Calif.

[73] Assignee: The United States of America as represented by the Secretary of the Air Force, Washington, D.C.

[21] Appl. No.: 865,271

[22] Filed: Dec. 28, 1977

[51] Int. Cl.$^2$ .......................... C10M 1/44; C07F 9/22; C07F 9/65

[52] U.S. Cl. ................................ 260/551 P; 252/49.9; 252/400 A

[58] Field of Search ......................... 260/551 P, 543 P

[56] References Cited

U.S. PATENT DOCUMENTS

| | | | |
|---|---|---|---|
| 3,463,813 | 8/1969 | Dickerson | 260/551 P |
| 3,522,303 | 7/1970 | Ulrich | 260/551 P |
| 3,644,456 | 2/1972 | Ulrich | 260/551 P X |
| 4,006,203 | 2/1977 | Chance et al. | 260/551 P X |

FOREIGN PATENT DOCUMENTS 2166498  9/1973  France.

OTHER PUBLICATIONS

Kukhar et al., CA 84:180176c, (1976).
Schoening et al., CA 86:171396p, (1977).
Kukhar et al., CA 85:192681x, (1976).
Kukhar et al., CA 82:4216r, (1975).

*Primary Examiner*—Thomas Waltz
*Attorney, Agent, or Firm*—Joseph E. Rusz; William J. O'Brien

[57] ABSTRACT

A method for synthesizing monophospha-s-triazines by effecting a reaction between an amidoylamidine and a trihalo-phosphorane.

5 Claims, No Drawings

MONOPHOSPHA-S-TRIAZINES

STATEMENT OF GOVERNMENT INTEREST

The invention described herein may be manufactured and used by or for the Government for governmental purposes without the payment of any royalty thereon.

BACKGROUND OF THE INVENTION

This invention concerns itself with a series of novel compounds and to a method for their preparation. More particularly, this invention relates to a method for the synthesis of a novel hetero-atom ring system, namely monophospha-s-triazines. The resulting compounds exhibit a broad range of properties and, depending on substituents, provide candidates for high temperature lubricants, hydraulic fluids, anti-oxidants, anti-corrosive agents and other applications which will become readily appreciated and apparent to those skilled in the art.

SUMMARY OF THE INVENTION

In the present invention, the synthesis of the novel monophospha-s-triazines of this invention is accomplished by effecting a reaction between (1) an amidoylamidine and (2) a pentavalent phosphorus halide which results in the formation of a phosphatriazine ring and a halogen halide as a reaction by-product. The reaction is allowed to continue at a temperature and for a period of time sufficient to complete the desired synthesis. Generally, specific reaction times and temperatures depend on the particular moieties employed as substituents in the amidoylamidine material. Reaction times of from 12 to 72 hours and temperatures of from 90° to 150° C. have been found suitable Accordingly, the primary object of this invention is to provide a novel method for synthesizing monophospha-s-triazines.

Another object of this invention is to provide a new series of compounds.

Still another object of this invention is to provide a series of novel monophospha-s-triazine compounds that exhibit extraordinary thermal and oxidative stability making them especially useful as fluids and lubricants under severe environmental conditions of high temperature and stress.

The above and still other objects and advantages of the present invention will become more readily apparent upon consideration of the following detailed description thereof.

DESCRIPTION OF THE PREFERRED EMBODIMENT

In accordance with this invention, it has been found that the above-noted objects can be accomplished by effecting a reaction between a mixture of a selected amidoylamidine and a trihalophosphorane. The reaction is affected at temperatures of from about 90° to 150° over a period of time from about 12 to 72 hours depending upon the specific reactants used in the reaction mixtures. The resulting monophospha-s-triazines are especially resistant to thermal and oxidating degradation and make excellent candidates for use as lubricants and fluids in high temperature and high stress situations.

Symmetrical triazines and their triphospha analogues, the trimeric phosphonitriles, have been studied extensively. A few examples of the intermediate diphospha-s-triazines have only recently been reported, whereas monophospha-s-triazines apparently are unknown. When substituted by perfluoroalkyl and/or perfluoroalkylether moieties, the s-triazines exhibit extraordinary thermal and oxidative stabilities. In addition, the perfluoroalkylether substituted triazines have very wide liquid ranges making them useful as fluids and lubricants under severe service condition. On the other hand, phosphorus compounds are known to increase lubricity and to inhibit corrosion under certain conditions.

It was believed, therefore, that it would be advantageous to combine these desirable properties and to synthesize novel compounds, such as monophospha-s-triazines, as candidates most promising to yield perfluorinated derivatives. After a considerable research effort, it was found that the method of this invention, in accomplishing the reaction of selected amidoylamidines with pentavalent phosphorus halides, did indeed produce the desired monophospha-s-triazine compounds.

The general synthesis contemplated by this invention is best illustrated by the following equation:

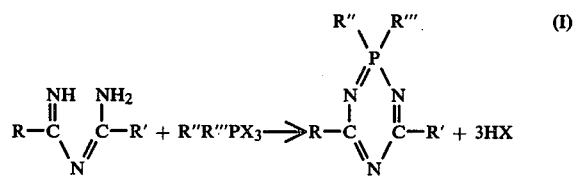

wherein an amidoylamidine is reacted with a pentavalent phosphorus halide at 90° to 150° C. giving concurrently with hydrogen halide evolution a phospha-s-triazine ring. The substituents R and R' can be the same or different and can be selected from perfluoroalkyl and perfluoroalkylether groups as represented by the general formulae $C_nF_{2n+1}$, $C_2F_5(OCF_2-CF_2)_nOCF_2$, $C_3F_7[OCF(CF_3)CF_2]_nOCF(CF_3)$, or and any combinations thereof which are readily apparent to those skilled in the art. The substituents R" and R''' on the phosphorus can be the same or different and can be either a halogen, i.e., chlorine, bromine, or fluorine or any of the following groups, i.e., perfluoroalkyl ($C_nF_{2n+1}$), aryl ($C_6H_5$), R-$C_6H_4$ (wherein R can be aromatic, alkyl, perfluoroalkyl or perfluoroalkylether moiety), perfluoroaryl ($C_6F_5$, $R_fC_6F_4$), perfluoroalkylether or any other type of a substituent as should be readily apparent to those skilled in the art. The substituent X on the phosphorus can be either chlorine, bromine or fluorine.

The following examples are presented to better illustrate the nature of the invention and how it may be carried into effect. Although these examples depict specific embodiments of the invention, they are not to be construed as limiting the scope of the invention in any way.

EXAMPLE 1

A mixture of N'-(perfluorooctanoylimidoyl)perfluorooctanoylamidine (1.76 g) and trichlorodiphenylphosphorane (0.65 g) was heated under nitrogen by-pass for 12 hr at 97°–100° C. The resulting product was boiled with heptane and filtered hot, giving on cooling 1.32 g (61.1% yield) of 1-diphenylphospha-3,5-bis(perfluoroheptyl)-2,4,6-triazine, mp, 73°–74.5° C.

Anal. Calcd, for $C_{28}H_{10}F_{30}N_3P$: C, 33.99; H, 1.02; F, 57.61; N, 4.25; P, 3.13; MW, 989.33; Found: C, 34.53; H, 1.16; F, 56.63; N, 4.52; P, 3.17; MW, 968.

The resulting triazine derivative of Example 1 is illustrated by the following structural formula:

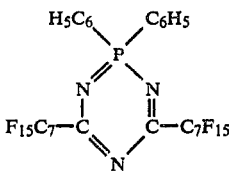

(II)

EXAMPLE 2

A mixture of the perfluoroalkylether-substituted amidoylamidine, $C_3F_7OCF(CF_3)CF_2OCF(CF_3)C(=NH)-N=C(NH_2)CF(CF_3)OCF_2CF(CF_3)OC_3F_7$ (3.13 g) and trichlorodiphenylphosphorane (1.02 g) was heated under nitrogen by-pass for 12 hr at 104°–110° C. The resulting product was distilled in vacuo giving 1-diphenylphospha-3,5-bis[$C_3F_7OCF(CF_3)CF_2$-$OCF(CF_3)$]-2,4,6-triazine, 2.69 g (72.6% yield), bp, 108°–111° C./0.001 mm (bp=355° C. at 760 mm; from DTA scan).

Anal. Calcd. for $C_{30}H_{10}F_{34}N_3O_4P$: C, 31.24; H, 0.87; F, 56.01; N, 3.64; P, 2.69; MW, 1153.35. Found: C, 31.56; H, 0.99; F, 56.84; N, 3.43; P, 2.51; MW, 1150.

The above diphenylphospha-3,5-bis$C_3F_7OCF(CF_3)CF_2OCF(CF_3)$-2,4,6-triazine was found to effectively inhibit oxidation of Krytox fluids (DuPont trade name, $F\text{-}[CF(CF_3)CF_2O]_n\text{-}C_2F_5$) and to prevent corrosion of M-50 ball bearing alloy by these fluids. A 1% by weight solution of this monophospha-s-triazine in Krytox decreased oxygen consumption and volatile products formation by a factor of over 60 during a 24 hr exposure to oxygen at 600° F. as compared to an identical treatment of the fluid in the absence of the additive. In addition, the M-50 coupon surface in the presence of the additive appeared unchanged whereas in the absence of any additive, under otherwise identical conditions, the surface becomes covered with deeply colored irregular deposits. These data are summarized below in Table I.

TABLE I

| | Degradation of Krytox Fluid in the Presence of M-50 Alloy Coupon at 600° F. in Oxygen for 24 Hr[a] | | | | |
|---|---|---|---|---|---|
| Fluid Used | | Oxygen Consumed | | Total Products Formed | |
| g | Additive | Total mg | mg/g[c] | mg | mg/g |
| 12.13 | none | 70.8 | 24.6 | 5.84 | 576.7 47.54 |
| 8.59 | 1% [e]$C_{30}H_{10}F_{34}O_4N_3P$ | 1.0 | 0.35 | 0.12 | 6.1 0.71 |

(a) The apparatus consisted of a sealed glass tube wherein the metal coupon was suspended in the fluid; the test was conducted in pure oxygen; at the conclusion of the test the oxygen was measured and the products were collected and measured. (b) Percent of oxygen available. (c) Oxygen consumed in mg/g Krytox employed. (d) Products formed in mg/g Krytox employed. (e) The percent is weight percent of additive per weight of Krytox fluid.

The above monophospha-s-triazine exhibited high thermal and thermal oxidative stability as shown by the recovery of 96.5 and 97% of the unchanged starting material, after 24 hr heat treatment at 325° in nitrogen and 24 hr at 235° in air, respectively.

EXAMPLE 3

A mixture of the perfluoroalkylether-substituted amidoylamidine $C_3F_7[OCF(CF_3)CF_2]_2OCF(CF_3)C(=NH)-N=C(NH_2)CF(CF_3)O[CF_2CF(CF_3)O]_2C_3F_7$ (4.11 g) and trichlorodiphenylphosphorane (1.07 g) was heated under nitrogen by-pass for 26 hr at 100°–105° C., 48 hr at 120° C., and 72 hr at 140° C. The resulting product was distilled in vacuo giving 1-diphenylphospha-3,5-bis[$C_3F_7[OCF(CF_3)CF_2]_2OCF(CF_3)$]-2,4,6-triazine, 2.44 g (52.1% yield), bp, 142°–148° C./0.001 mm (bp=383° C. at 760 mm; from DTA scan).

Anal. Calcd, for $C_{36}H_{10}F_{46}N_3O_6P$: C, 29.11; H, 0.68; F, 58.83; N, 2.83; P, 2.09; O, 6.46; MW, 1485.37. Found: C, 30.10; H, 0.98; F, 59.20; N, 2.82; P, 2.04; MW, 1510.

The products of Examples 2 and 3 are represented by the following structural formula in which the letter n represents the integer 1 in the case of Example 2 and the integer 2 in the case of Example 3.

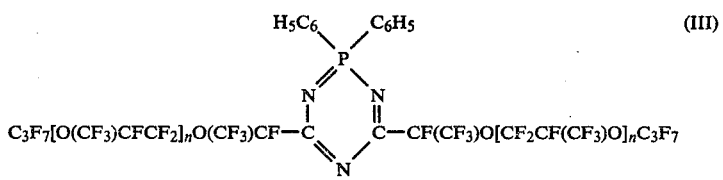

(III)

While the invention has been described with particularity in reference to specific embodiments thereof, it is to be understood that the disclosure of the present invention is for the purpose of illustration only and is not intended to limit the invention in any way, the scope of which is defined by the appended claims.

What is claimed is:

1. A method for synthesizing monophospha-s-triazine which comprises the steps of (1) forming a mixture of reaction ingredients composed of (a) an amidoylamidine and (b) a trihalophosphorane; (2) heating said ingredients for a period of time and at a temperature sufficient to effect a reaction therebetween; and (3) separating the resulting reaction product.

2. A process in accordance with claim 1 wherein said ingredients are heated to a temperature of from about 90° to 150° C. for a period of from about 12 to 72 hours.

3. The compound 1-diphenylphospha-3,5-bis(perfluoroheptyl)-2,4,6-triazine.

4. The compound 1-diphenylphospha-3,5-bis[$C_3F_7OCF(CF_3)CF_2OCF(CF_3)$]-2,4,6-triazine.

5. The compound 1-diphenylphospha-3,5-bis[$C_3F_7[OCF(CF_3)CF_2]_2OCF(CF_3)$]-2,4,6-triazine.

* * * * *